United States Patent [19]
Ideker

[11] Patent Number: 5,873,896
[45] Date of Patent: Feb. 23, 1999

[54] CARDIAC DEVICE FOR REDUCING ARRHYTHMIA

[75] Inventor: Raymond E. Ideker, Birmingham, Ala.

[73] Assignee: UAB Research Foundation, Birmingham, Ala.

[21] Appl. No.: 864,030

[22] Filed: May 27, 1997

[51] Int. Cl.$^6$ .................................................. A61N 1/362
[52] U.S. Cl. .................................................. 607/14
[58] Field of Search ........................ 607/5, 6, 10, 14, 607/122, 129

[56] References Cited

U.S. PATENT DOCUMENTS

| | | | |
|---|---|---|---|
| 3,937,226 | 2/1976 | Funke .................................. | 607/14 |
| 3,939,844 | 2/1976 | Pequignot ........................... | 607/14 |
| 4,554,922 | 11/1985 | Prystonsky et al. ................. | 607/14 |
| 5,002,052 | 3/1991 | Haluska .............................. | 128/419 |
| 5,018,522 | 5/1991 | Mehra ................................. | 607/10 |
| 5,107,834 | 4/1992 | Ideker et al. ....................... | 128/419 |
| 5,111,811 | 5/1992 | Smits .................................. | 128/419 |
| 5,191,885 | 3/1993 | Bilof et al. .......................... | 607/14 |
| 5,243,978 | 9/1993 | Duffin, Jr. ........................... | 607/11 |
| 5,350,404 | 9/1994 | Adams et al. ...................... | 607/5 |
| 5,411,547 | 5/1995 | Causey, III ......................... | 607/129 |

OTHER PUBLICATIONS

Radiofrequency Current Ablation of Thin–walled Structures: an in Vitro Study Comparing Unipolar and Bipolar Electrode Configuration. Ole–Gunnar Anfinsen, MD, Erik Kongsgaard, MD, Halfdan Aass, MD, Jan P. Amlie, MD. Rikshospitalet, Oslo, Norway, NASPE Abstracts, Apr. 1996, Part II, PACE, vol. 19, p. 714.

Maximal Interelectrode Spacing Requirements for Creating Continuous Myocardial Lesions Using Multielectrode Catheters. Deeptankar Demazumder BS, Stephen M. Dillon, PhD, Charles D. Gottlieb, MD, David J. Callans, MD, James E. Wilson, PhD, Francis E. Marchlinski, MD, David Schwartzman, MD. Philadelphia Heart Inst., PA. NASPE Abstracts, Apr. 1996, Part II, PACE, vol. 19 p. 714.

Mechanism of Cardiac Defibrillation in Open–Chest Dogs With Unipolar DC–Coupled Simultaneous Activation and Shock Potential Recordings. Francis X. Witkowski, MD, Patricia A. Penkoske, MD, and Robert Plonsey, PhD. From the Departments of Medicine (F.X.W.), Pediatrics (P.A.P.), and Surgery (P.A.P.), University of Alberta School of Medicine, Edmonton, Alberta, Canada, and the Department of Biomedical Engineering (R.P.), Duke University, Durham, North Carolina. Circulation, vol. 82, No. 1, Jul. 1990, pp. 244–260.

*Primary Examiner*—William E. Kamm
*Attorney, Agent, or Firm*—Gifford, Krass, Groh, Sprinkle, Patmore, Anderson & Citkowski, P.C.

[57] ABSTRACT

A device is disclosed for reducing the likelihood of cardiac arrhythmia or halting the arrhythmia after it begins without having to give a large shock which can be painful or may damage the heart. The device includes an elongated primary strip having a plurality of electrodes positioned at spaced intervals along its length. The strip is dimensioned so that, upon insertion into a patient, the electrodes on the strip electrically contact the heart tissue, either directly or through an intermediate high resistance conductive layer. The electrodes are then energized with an electrical energy sufficient to hyperpolarize heart tissue adjacent to each of the electrodes. Furthermore, the electrodes are spaced along the strip sufficiently close to each other so that, upon energization of the electrodes, a line of heart tissue is hyperpolarized to thereby prevent cardiac electrical conductance across that line. Optionally, secondary electrode strip(s) extend alongside, or encircle, the primary strip. The secondary strip(s) include electrodes which are activated by lower current levels than the primary strip to minimize the likelihood of an activation front caused by activation from the primary strip electrodes.

31 Claims, 2 Drawing Sheets

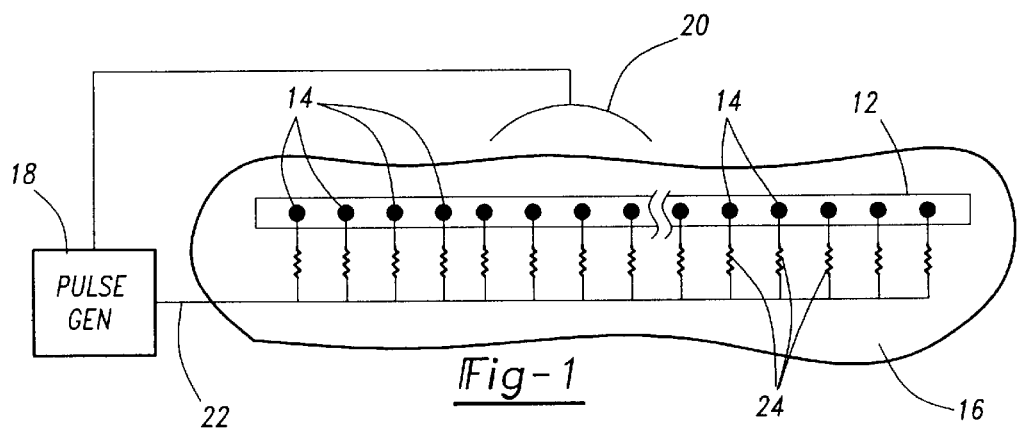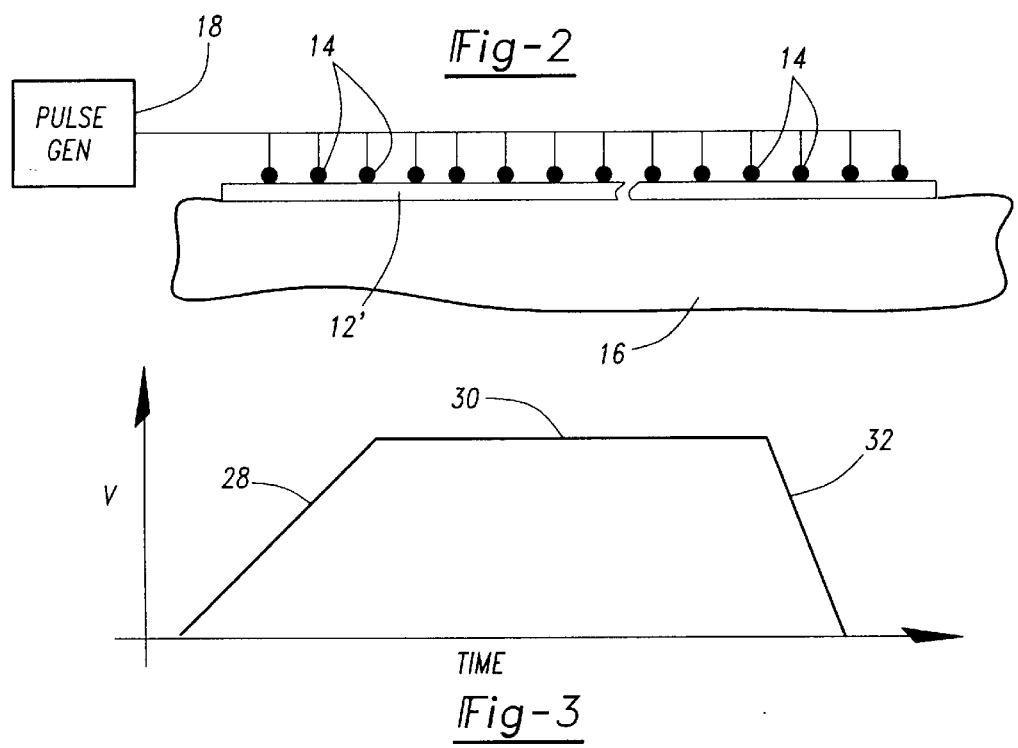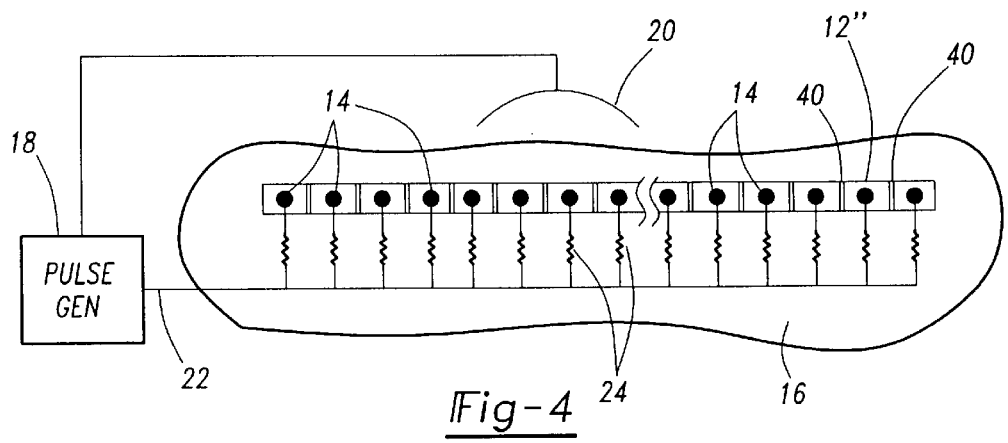

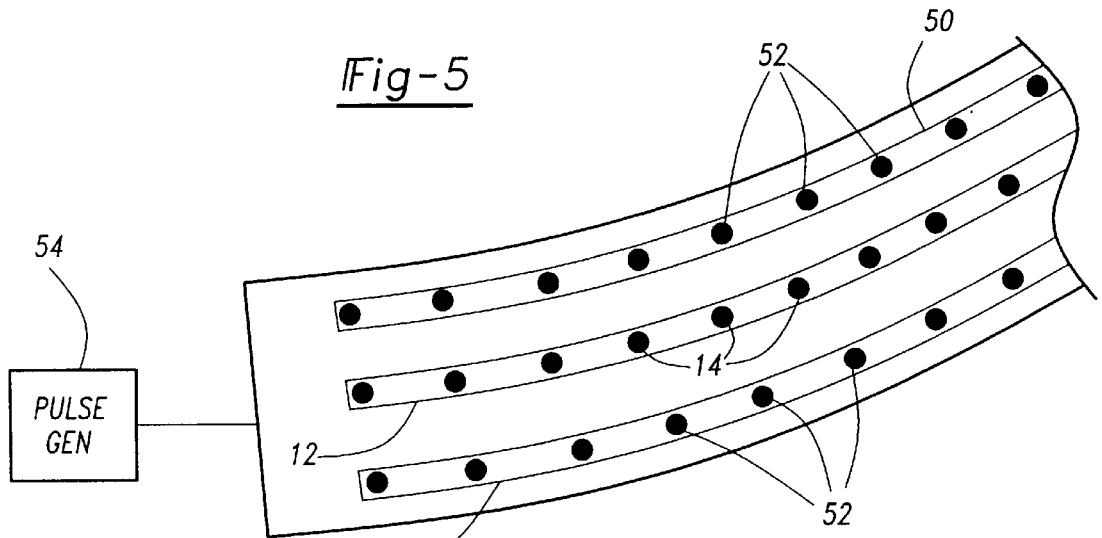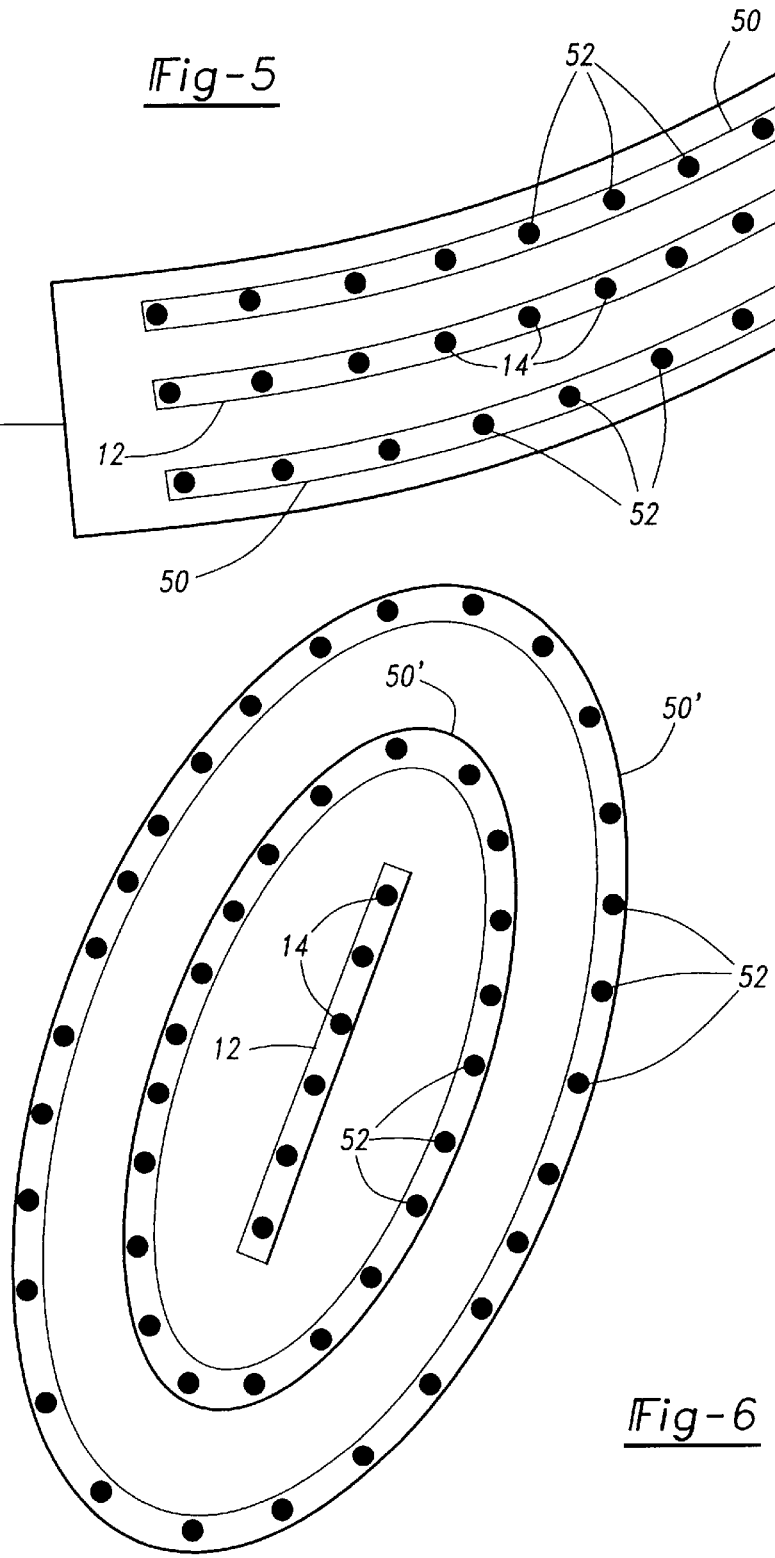

CARDIAC DEVICE FOR REDUCING ARRHYTHMIA

BACKGROUND OF THE INVENTION

I. Field of the Invention

The present invention relates generally to medical devices and, more particularly, to a medical device to reduce the likelihood of cardiac arrhythmia or to halt it once it has begun.

II. Description of the Prior Art

It is well known that, in order to halt tachyrhythmia, defibrillators are employed to apply a shock to the heart. While this previously known method is effective in halting tachyrhythmia, this procedure is oftentimes quite painful for the patient. This is particularly true for atrial fibrillation since patients normally do not lose consciousness with this type of arrhythmia. Furthermore, shocks having an energy level of 1 to 5 joules are oftentimes required to halt atrial fibrillation while electrical shocks greater than a fraction of a joule are quite painful.

In the treatment of arrhythmia, such as tachyrhythmia, it is believed that a certain critical mass of myocardium must be present in order to allow the fibrillation to be maintained. In one previously known procedure known as the maze procedure, the heart tissue is surgically divided into segments, each of which is smaller than the critical mass of myocardium necessary to maintain a fibrillation. The maze procedure, however, while effective in use, requires open heart surgery and entails relatively high risk to the patient. Furthermore, the previously known maze procedure creates a permanent surgical modification to the heart which may have long term undesirable effects which are currently unknown. Likewise, the use of the maze procedure may preclude future medical treatments for arrhythmia which would otherwise be beneficial to the patient.

SUMMARY OF THE PRESENT INVENTION

The present invention provides a device for reducing the likelihood of arrhythmia or halting it after it has begun which overcomes all of the abovementioned disadvantages of the previously known procedures.

In brief, the device of the present invention comprises an elongated primary strip having a plurality of electrodes positioned at spaced intervals along its length. The strip is dimensioned so that, upon insertion into a patient, the electrodes on the strip are in electrical contact with the heart tissue either directly or indirectly through an intermediate conductive layer.

Means are then provided for electrically energizing the electrodes as anodes with electrical energy sufficient to hyperpolarize heart tissue adjacent to each of the electrodes. Furthermore, the electrodes are spaced sufficiently close together to each other along the strip so that, upon energization of the electrodes, a line of heart tissue is hyperpolarized to thereby prevent cardiac electrical conductance across the line thereby preventing, or at least reducing the likelihood of, arrhythmia. If an arrhythmia is present, the electrodes are energized for a brief period to halt the arrhythmia. In effect, energization of the electrodes divides the myocardium into segments, each having a critical mass insufficient to maintain a fibrillation.

Since a plurality of electrodes is energized to create the line of hyperpolarized heart tissue, only relatively low energy levels are necessary to energize each of the individual electrodes. This relatively low energy level causes, at most, minor discomfort to the patient.

Furthermore, the energy level to activate the electrodes is selected so that it is too low to cause permanent damage or alteration to the heart tissue. It is known that while tissue immediately beneath these anodal electrodes will be hyperpolarized, tissue just a few millimeters away from this electrode will be depolarized. The magnitude of this depolarization is less than the magnitude of the hyperpolarization immediately beneath the electrode. If the magnitude of the depolarization is sufficiently great, an activation front will be initiated in this region that can propagate to maintain or reinduce an arrhythmia. Thus, the energy level used to activate the electrodes is selected so that it is sufficiently large to cause the hyperpolarization immediately beneath the electrode to be great enough to block the transit of activation fronts beneath the electrode, yet is not so great as to cause the depolarization a few millimeters away to be large enough to initiate new activation fronts.

Optionally one or more secondary strips, each having a plurality of spaced electrodes, are provided alongside or encircle the primary strip. The secondary strip electrodes are similar in construction to the primary strip. However, in use the secondary strip electrodes are energized at a current level lower than the primary strip to minimize the likelihood of an activation front caused by energization of the primary strip electrodes. The secondary strips will also be energized as anodes and will be located adjacent to and a few millimeters away from the primary strip in the region in which maximum depolarization is expected to be created when the primary strip is energized by itself. By energizing these secondary strips as anodes to a lower level than the primary strip, these depolarized regions will be neutralized or slightly hyperpolarized and the depolarized region will be moved a few millimeters farther away from the primary strip where this depolarization will cover a larger area and will have a smaller peak magnitude than the peak magnitude of depolarization generated by the primary strip alone. By decreasing the peak magnitude of depolarization, the secondary strips will better allow the primary strip to be energized to a level that should block activation fronts in the immediately subjacent hyperpolarized tissue without giving rise to new activation fronts in the adjacent depolarized tissue.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which:

FIG. 1 is a diagrammatic view illustrating a preferred embodiment of the present invention;

FIG. 2 is a view similar to FIG. 1 but illustrating a modification thereof;

FIG. 3 is a graph illustrating the energization of the electrodes of the preferred embodiment of the present invention;

FIG. 4 is a view similar to FIG. 1 but illustrating a modification thereof;

FIG. 5 is an elevational view illustrating a still further preferred embodiment of the invention; and FIG. 6 is a view similar to FIG. 5 but illustrating a still further preferred embodiment of the invention.

DETAILED DESCRIPTION OF A PREFERRED EMBODIMENT OF THE PRESENT INVENTION

With reference first to FIG. 1, a preferred embodiment of the device 10 of the present invention to reduce the likelihood of arrhythmia is there shown and comprises an elongated strip 12. A plurality of electrical electrodes 14 are positioned at spaced intervals, e.g. 1–4 millimeters, along the length of the strip 12.

The strip 12 is positioned in the patient's body so that, upon insertion, the electrodes 14 electrically contact heart tissue 16. Furthermore, the heart tissue 16 can be either an atrium or ventricle and the strip 12 may be either positioned on the endocardium or epicardium.

The electrodes 14 are electrically connected to the anode of a pulse generator 18 while a cathode 20 for the pulse generator 18 is electrically connected to the patient at a position spaced from the heart, for example the can of the pulse generator.

As shown in FIG. 1, a single electrical line 22 electrically connects the anode from the pulse generator 18 to the electrodes 14. However, in order to ensure that each electrode 14 receives substantially the same amount of electrical energy, a small resistive element 24 is preferably operatively positioned between the common line 22 and each electrode 14.

With reference now to FIGS. 1 and 3, the pulse generator 18 preferably generates a trapezoidal output pulse illustrated in FIG. 3. The trapezoidal output pulse includes an ascending initial ramp portion 28 followed by a plateau 30 and a descending ramp portion 32. Preferably, both the ascending and descending ramps have a duration between zero and two seconds while the plateau has a duration up to thirty seconds.

The use of a trapezoidal waveform such as illustrated in FIG. 3 by eliminating abrupt current changes as would be present, e.g. in a square waveform, serves to accommodate the muscle tissue and minimize the likelihood of tissue stimulation and activation of new fronts. The use of a trapezoidal waveform also reduces discomfort, if any, to the patient.

In operation, during arrhythmia, the pulse generator 18 is activated to simultaneously energize all of the electrodes 14 with the trapezoidal waveform illustrated in FIG. 3. The electrodes 14, furthermore, are sufficiently close together so that, upon energization by the waveform 30, the electrodes hyperpolarize not only the heart tissue beneath each electrode 14, but also the heart tissue between adjacent electrodes 14. In doing so, the device 10 creates a line of hyperpolarized heart tissue such that cardiac electrical conductance across the hyperpolarized line of tissue is prevented. Thus, activation of the electrodes 14 by the pulse generator 18 effectively divides the myocardium into segments having less than the critical mass necessary to sustain an arrhythmia.

The energization of the electrodes 14 by the pulse generator 18, as discussed above, is sufficiently high to hyperpolarize the tissue beneath and between the electrodes. However, the energy level of the pulse generator 18 is also selected such that it does not permanently damage the heart tissue nor cause extreme depolarization of heart tissue a predetermined distance, e.g. 1–4 millimeters, away from the electrodes 14. Such extreme depolarization could disadvantageously result in a new activation source.

In the preferred embodiment of the invention, each of the electrodes 14 is energized in the range of 0.01 to 10 milliamps per pulse.

With reference now to FIG. 2, a modification of the present invention is there shown. Referring then to FIG. 2, the strip 12' is formed from a high resistance conductive material which is in contact with the heart tissue 16. The electrodes 14, on the other hand, are positioned on the side of the strip 12' away from the heart tissue 16.

In operation, the conductive strip 12' forms an intermediate layer or buffer between the electrodes 14 and the heart tissue 16 to minimize voltage gradients imparted to the heart tissue 16 between adjacent electrodes 14.

With reference now to FIG. 4 a still further preferred embodiment of the strip 12" is there shown. The strip 12" is identical to the strip 12 (FIG. 1) except that an electrical insulating layer 40 is provided between adjacent electrodes 14. The insulating layers 40 ensure that the current flowing from the electrodes to the tissue remains substantially constant along the entire length of the strip 12".

Referring now to FIG. 5, a still further embodiment of the present invention is there shown in which a secondary strip 50 is provided on each side of the main strip 12 (or 12' or 12") such that the secondary strips 50 are spaced from the strip 12 by a few millimeters. The secondary strips 50 are substantially identical to the main strip 12. As such, each secondary strip 50 has a plurality of spaced electrodes 52 along its length which are electrically energized by a pulse generator 54 in synchronization with the energization of the electrodes 14 on the main strip 12. Indeed the pulse generator 54 is also preferably used to also energize the electrodes 14 on the main strip 12. The electrical current supplied to each electrode 52 of the secondary strips 50 by a pulse generator 54, however, is less than the current to each electrode 14 on the strip 12. Consequently, the secondary strips 50 serve to extend the area of hyperpolarization and simultaneously cancel depolarization of the tissue.

FIG. 6 illustrates still a further embodiment of the invention in which one or more secondary strips 50' are provided around and spaced outwardly from the main strip 12 (or 12' or 12"). The secondary strips 50' are substantially identical to and energized in the same manner as the secondary strips 50 in FIG. 5 except that the secondary strips 50' completely enclose the main strip 12. Such a configuration minimizes the likelihood of new fronts potentially caused by end effects of the main strip 12.

From the foregoing, it can be seen that the present invention provides a simple and yet effective device for reducing the likelihood of arrhythmia without permanent or irreversible damage to the heart. Furthermore, since a relatively small electrical energy is provided to each of the electrodes, only minor discomfort, if any discomfort at all, is caused to the patient during defibrillation.

Having described our invention, however, many modifications thereto will become apparent to those skilled in the art to which it pertains without deviation from the spirit of the invention as defined by the scope of the appended claims.

We claim:

1. A device for reducing the likelihood of arrhythmia comprising:

an elongated main strip, said strip having a plurality of electrodes, said electrodes being positioned at spaced intervals along the strip, said strip being dimensioned so that, upon insertion into a patient, said electrodes on said strip electrically contact heart tissue, means for electrically energizing said electrodes with electrical energy sufficient to hyperpolarize heart tissue adjacent each of said electrodes, wherein said electrodes are spaced along said strip sufficiently close to each other so that, upon energization of said electrodes, a line of heart tissue is hyperpolarized to thereby prevent cardiac electrical conductance across said line.

2. The invention as defined in claim 1 wherein each of said electrodes comprises an anode.

3. The invention as defined in claim 1 wherein said strip extends between two cardiac areas.

4. The invention as defined in claim 1 wherein said energizing means comprises means for simultaneously energizing said electrodes.

5. The invention as defined in claim 1 wherein said energizing means are activated at a voltage level less than a level which initiates an activation front at a position spaced from each said electrode.

6. The invention as defined in claim 1 wherein the heart tissue is an atrium.

7. The invention as defined in claim 1 wherein the heart tissue is a ventricle.

8. The invention as defined in claim 1 wherein the strip is positioned on the epicardium of the heart tissue.

9. The invention as defined in claim 1 wherein the strip is positioned on the endocardium of the heart tissue.

10. The invention as defined in claim 1 wherein said energizing means comprises means to energize said electrodes with a trapezoidal waveform having an ascending ramp upon energization followed by a plateau and descending ramp.

11. The invention as defined in claim 10 wherein said ascending and descending ramps have a duration between zero and two seconds.

12. The invention as defined in claim 10 wherein said plateau has a duration up to thirty seconds.

13. The invention as defined in claim 1 wherein each electrode is energized by a current pulse between 0.01 milliamps and 10 milliamps.

14. The invention as defined in claim 1 and further comprising a high resistance conductive layer interposed between said electrodes and the heart tissue.

15. The invention as defined in claim 1 and further comprising an electrical insulating layer provided between adjacent electrodes on said strip.

16. The invention as defined in claim 1 and further comprising:

at least one elongated secondary strip, said secondary strip having a plurality of electrodes, said electrodes being positioned at spaced intervals along said secondary strip, said secondary strip being dimensioned so that, upon insertion into a patient, said electrodes on said strip electrically contact heart tissue at a position spaced from and alongside said main strip, and means for electrically energizing said electrodes on said secondary strip in synchronization with the energization of the electrodes on said main strip.

17. The invention as defined in claim 16 and comprising two said secondary strips.

18. The invention as defined in claim 16 wherein said at least one secondary strip completely surrounds said main strip.

19. The invention as defined in claim 16 wherein said means for energizing said electrodes on said secondary strip provides less current per electrode than the means to energize the electrodes on said main strip.

20. A method for reducing the likelihood of arrhythmia comprising the steps of:

inserting an elongated strip having a plurality of electrodes at spaced intervals along the strip into a patient so that said electrodes on said strip electrically contact heart tissue, electrically energizing said electrodes with electrical energy sufficient to hyperpolarize heart tissue adjacent each of said electrodes, wherein said electrodes are spaced along said strip sufficiently close to each other so that, upon energization of said electrodes, a line of heart tissue is hyperpolarized to thereby prevent cardiac electrical conductance across said line.

21. The invention as defined in claim 20 wherein said energizing step comprises the step of simultaneously energizing said electrodes.

22. The invention as defined in claim 20 wherein said energizing step comprises the step of activating the electrodes at a voltage level less than a level which initiates an activation front at a position spaced from each said electrode.

23. The invention as defined in claim 20 wherein said inserting step comprises the step of inserting the strip into an atrium.

24. The invention as defined in claim 20 wherein said inserting step comprises the step of inserting the strip into a ventricle.

25. The invention as defined in claim 20 wherein said inserting step comprises the step of positioning the strip on the epicardium of the heart tissue.

26. The invention as defined in claim 20 wherein said inserting step comprises the step of positioning the strip on the endocardium of the heart tissue.

27. The invention as defined in claim 20 wherein said energizing step comprises the step of energizing said electrodes with a trapezoidal waveform having an ascending ramp upon energization followed by a plateau and descending ramp.

28. The invention as defined in claim 20 wherein said energizing step comprises the step of energizing each electrode by a current pulse between 0.01 milliamps and 10 milliamps.

29. The invention as defined in claim 20 and further comprising the steps of:

inserting at least one elongated secondary strip, said secondary strip having a plurality of electrodes at spaced intervals along said secondary strip into a patient, said electrodes on said strip electrically contact heart tissue at a position spaced from and alongside said first mentioned strip, and electrically energizing said electrodes on said secondary strip in synchronization with the energization of the electrodes on the first mentioned strip.

30. The invention as defined in claim 29 wherein said step of inserting the secondary strip into the patient comprises the step of positioning said secondary strip so that said secondary strip completely surrounds said first mentioned strip.

31. The invention as defined in claim 29 and comprising the step of energizing said electrodes on said secondary strip at a lesser current per electrode than the step of energizing the electrodes on said first mentioned strip.

* * * * *